United States Patent
Spencer

Patent Number: 5,928,216
Date of Patent: *Jul. 27, 1999

[54] SURGICAL/MEDICAL TUBING AND CONTAINERS FOR USE IN CONVEYING MEDICAL SOLUTIONS AND THE LIKE

[75] Inventor: Dudley W. C. Spencer, Wilmington, Del.

[73] Assignee: Denco, Inc., Wilmington, Del.

[*] Notice: This patent is subject to a terminal disclaimer.

[21] Appl. No.: 08/790,192

[22] Filed: Jan. 30, 1997

[51] Int. Cl.⁶ .................................................. A61M 25/00
[52] U.S. Cl. ........................... 604/523; 604/264; 604/265
[58] Field of Search ..................... 604/93, 264, 280–283, 604/265, 523–539; 138/118; 525/173, 175, 176; 428/36.8, 36.9, 36.92, 480

[56] References Cited

U.S. PATENT DOCUMENTS

| | | |
|---|---|---|
| 4,010,222 | 3/1977 | Shih . |
| 4,048,254 | 9/1977 | Hillier et al. . |
| 4,219,628 | 8/1980 | Weemes et al. . |
| 4,322,335 | 3/1982 | Nield . |
| 4,337,947 | 7/1982 | Saito et al. . |
| 4,344,874 | 8/1982 | Akagi et al. . |
| 4,616,064 | 10/1986 | Zukosky et al. . |
| 4,628,072 | 12/1986 | Shiraki et al. . |
| 4,657,970 | 4/1987 | Shiraki et al. . |
| 4,670,510 | 6/1987 | Kobayashi et al. . |
| 4,680,344 | 7/1987 | Coker . |
| 4,778,842 | 10/1988 | Taniguchi et al. . |
| 4,806,588 | 2/1989 | Fujimoto et al. . |
| 4,816,343 | 3/1989 | Mueller et al. . |
| 4,820,768 | 4/1989 | Shiraki et al. . |
| 4,861,830 | 8/1989 | Ward, Jr. . |
| 4,868,243 | 9/1989 | Gelles et al. . |
| 4,906,687 | 3/1990 | Modic . |
| 4,914,152 | 4/1990 | Miyashita et al. . |
| 4,954,568 | 9/1990 | Gelles et al. . |
| 4,968,464 | 11/1990 | Kojoh et al. . |
| 5,089,553 | 2/1992 | Umeda et al. . |
| 5,091,459 | 2/1992 | Howe . |
| 5,112,915 | 5/1992 | Morelli et al. . |
| 5,115,012 | 5/1992 | Howe . |
| 5,453,099 | 9/1995 | Lee et al. . |
| 5,496,291 | 3/1996 | Spencer ................................. 604/264 |
| 5,733,268 | 3/1998 | Spencer ..................................... 604/93 |

OTHER PUBLICATIONS

Research Disclosure, May 1989, pp. 329–330, No. 301, XP000052490, Blends of Polyester–Ethers with Ethylene––Acrylic Acid Copolymers.

Primary Examiner—Ronald Stright
Attorney, Agent, or Firm—Connolly & Hutz

[57] ABSTRACT

An ionomeric modified poly-ether-ester plastic material combined with a small amount of silica is used as a substitute for the conventional uses of polyvinylchloride in such applications as tubing for medical applications, for bags and other medical containers, for tubing in food processing and as sheets and films for bacterial and virus exclusion. The ionomeric modified poly-ether-ester has various advantages which make it particularly suitable for such uses. The silica may be in the form of colloidal silica dioxide or silica oil.

27 Claims, 4 Drawing Sheets

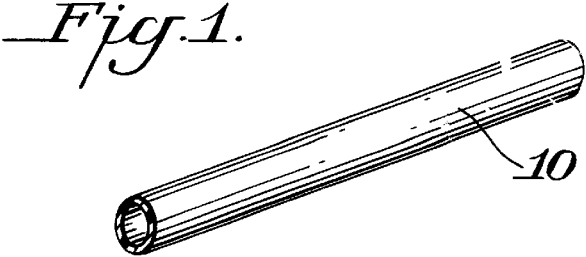
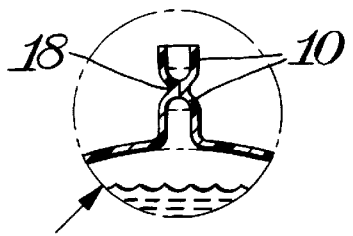
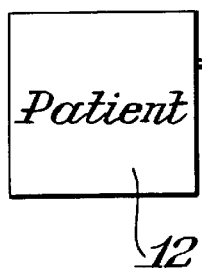 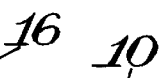 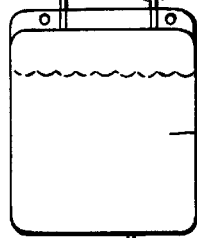
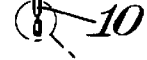
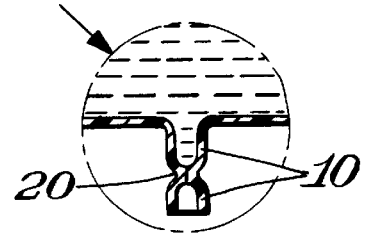

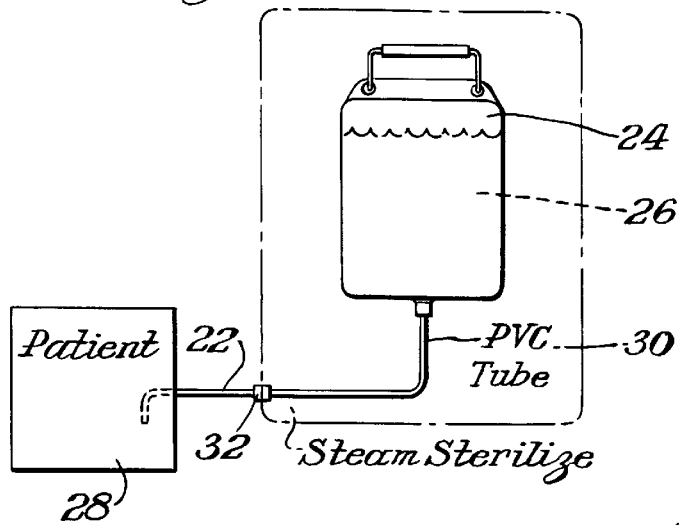
Fig.5.(PriorArt)
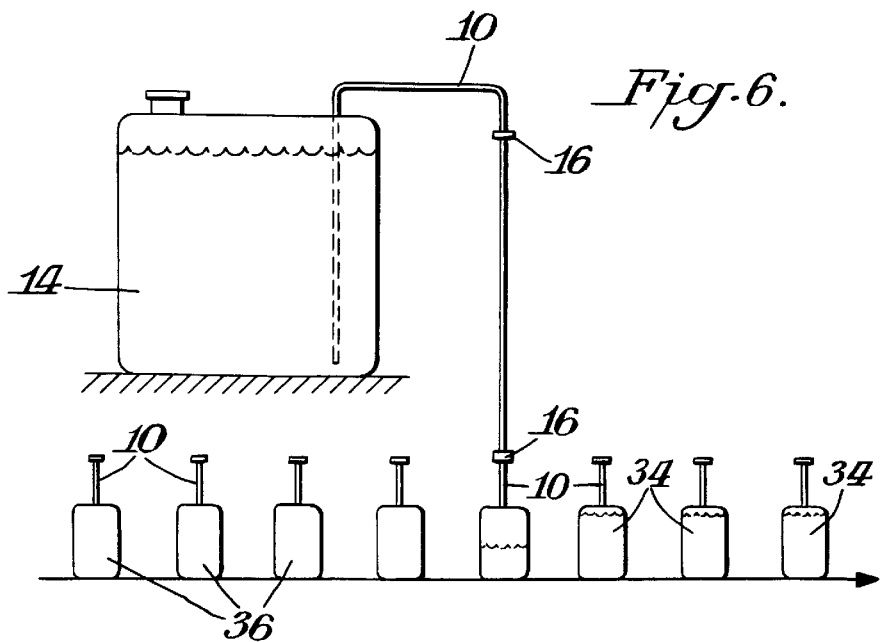
Fig.6.
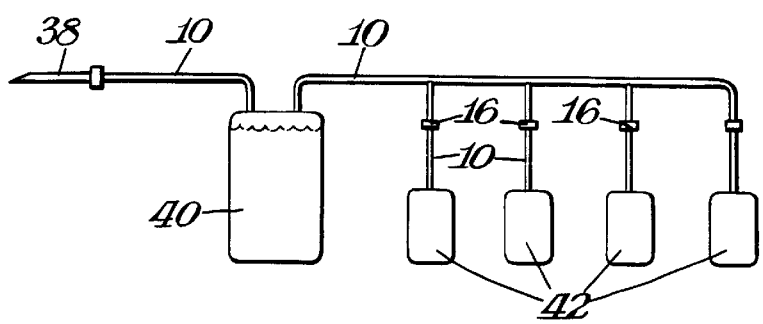
Fig.7.

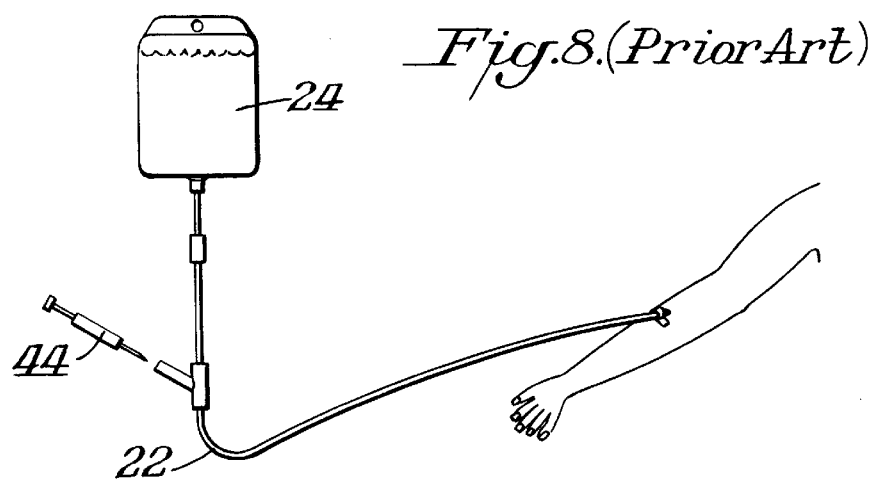
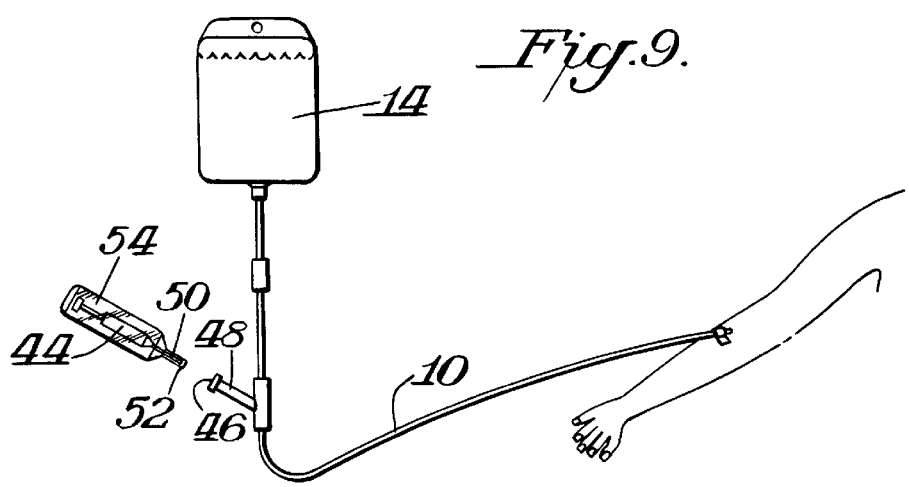
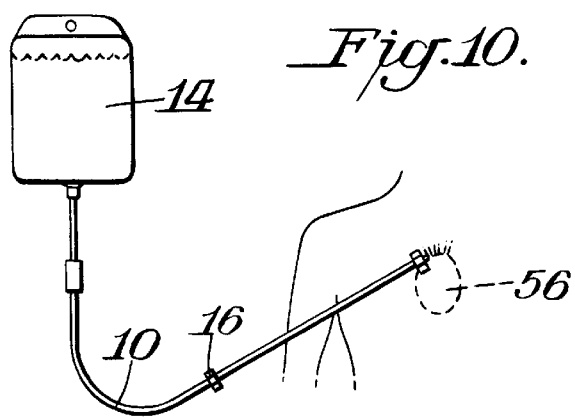

SURGICAL/MEDICAL TUBING AND CONTAINERS FOR USE IN CONVEYING MEDICAL SOLUTIONS AND THE LIKE

BACKGROUND OF THE INVENTION

Polyvinylchloride (PVC) is the accepted material for use as tubing in various medical applications, such as peritoneal dialysis, blood processing, chemotherapy and other uses. In such uses, a consumable is conveyed through the tubing from one location to another. For peritoneal dialysis (CAPD), for example, it is also the practice to replace a used dialysate bag with a new bag. This is accomplished by cutting through the PVC tubing leading from the used bag and then welding tubing from a new bag to the cut portion of the tubing so that one bag may replace another. PVC is also the generally accepted material for forming bags and other medical containers and is commonly used as tubing in food processing particularly for fluids and semi-solids. In addition, PVC is the material generally used for forming sheets and films for bacterial and virus exclusion. Despite its acceptance by the art, PVC has a number of disadvantages which would be desirable to overcome in such uses. For example, conventional PVC includes a plasticizer (DOP) which might leach into the solutions in the bag. Further, after PVC has leached its DOP, large volumes of PVC particulates are released. Other disadvantages will be later referred to.

In my U.S. Pat. No. 5,496,291 I disclose an ionomeric modified poly-ether-ester material which could be used as a substitute for polyvinylchloride.

SUMMARY OF THE INVENTION

An object of this invention is to provide a material which will act as an improved replacement for PVC in the conventional uses of PVC.

A further object of this invention is to provide such a material which can be used as tubing for medical applications, as bags and other medical containers, for tubing food processing and as sheets and films for bacterial and virus exclusion.

In accordance with this invention the material which meets the above objects includes an ionomeric modified poly-ether-ester as described in my U.S. Pat. No. 5,496,291. Unlike the patent, however, the material also includes a small or minor amount of silica which may be in the form of colloidal silica dioxide or silica oil.

THE DRAWINGS

FIG. 1 is a perspective view of a tube made from ionomeric modified poly-ether-ester and polyvinylchloride in accordance with this invention;

FIG. 2 is a schematic view of a urinary drainage system utilizing the tubing of FIG. 1;

FIG. 2A is an enlarged cross-sectional view of a top air seal shown in the corresponding circled portion of FIG. 2;

FIG. 2B is an enlarged cross-sectional view of a discharge line in the corresponding circled portion of FIG. 2;

FIG. 5 is a schematic view of a prior art system for steam sterilizing when using PVC tubing in peritoneal dialysis;

FIG. 6 is a schematic view showing a sterile solution fed to sterile bags using the material of this invention;

FIG. 7 is a schematic view showing a primary blood bag and four satellite bags connected by the tubing of this invention as used in blood processing;

FIG. 8 is a schematic view showing prior art chemotherapy treatment using PVC tubing;

FIG. 9 is a view similar to FIG. 8 showing use of the tubing of this invention; and FIG. 10 is a schematic view showing parenteral feeding of the body using the tubing of this invention.

DETAILED DESCRIPTION

Figure 3:
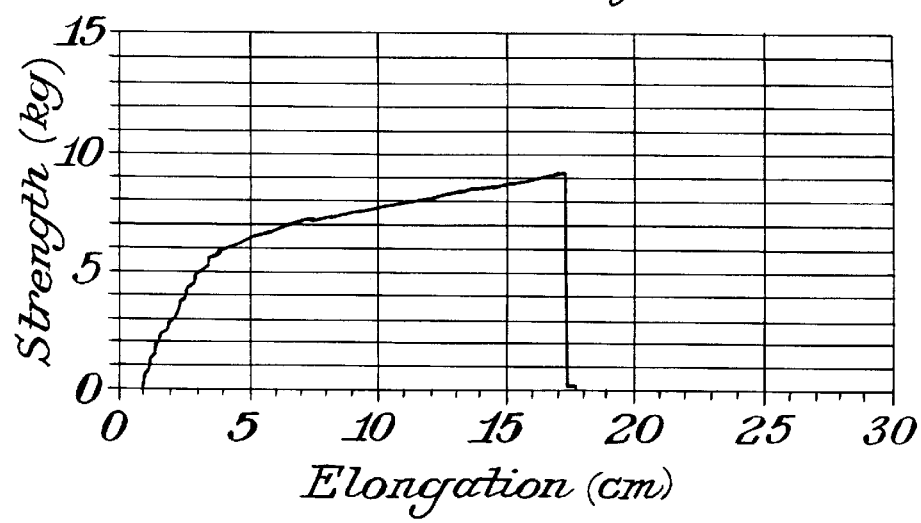
FIGS. 3–4 are graphs comparing the elongation and strength characteristics of polyvinylchloride welded to ionomeric modified poly-ether-ester material invention (FIG. 3) and of the ionomeric modified poly-ether-ester alone (FIG. 4)

The present invention is directed to providing a material which can be used as a substitute for PVC in the conventional uses of PVC while having advantages over such PVC material. The material of this invention is an ionomeric modified poly-ether-ester with a small amount of silica. Poly-ether-ester is a well known material generally used to take advantage of its high strength characteristics. Such material is used, for example, in clothing generally referred to as polyester clothing. Ordinarily, the strength of such material would make it unsuitable for use as a substitute for PVC in the uses of PVC with which this invention deals. It has been discovered, however, that the poly-ether-ester material can be modified by incorporation of a small amount of an ionomer which would modify the characteristics of the poly-ether-ester by giving it sufficient fragility to, for example, permit the material when used as a sealed tube to pop open. The specific amount of ionomer would depend upon the end use. The qualities are retained when the material is mixed with a small amount of silica, such as colloidal silica dioxide (amorphous or pharmaceutical grade). The silica may be in the form of silica oil.

In general, the ionomeric modifier comprises from 0.5–50% by weight and preferably from 1% to 25% by weight of the combination depending upon the end use requirement. For example, in tubing such as for CAPD use where the material is to be sealed, welded and the lumen reopened the broad ionomer composition range would be 2% to 15% by weight, a more preferred range of 3%–10% by weight. A range of 7–10% by weight is ideal. The result is a tube which is strong, sufficiently rubber like, and a degree of fracture to make reopening of the sealed tubes by finger pressure. For bags, films and other thin structures the ionomer would be present in a range of from 1% to 50% by weight of the combination depending on the end use requirements. For food processing tubes and aseptic surgical draping procedures a range of 10% to 20% by weight is desirable. For implanted catheters and sutures the range of 0.5 to 1% by weight is preferred.

The material of this invention is a combination of silica and an ionomeric modified poly-ether-ester wherein the material has from 5% to 10% by weight silica oil or from 1% to 3% by weight colloidal silica dioxide mixed with from 1% to 50% by weight ionomer and from 50% to 99% by weight poly-ether-ester with equal mixtures of ionomer and poly-ether-ester being feasible. The basic material components are as follows:

Poly-ether-ester

POLY-ETHER-ESTER BLOCK COPOLYMER (Block poly-ether-ester) (Co-poly-ether-ester) (Polyester elastomer) (Thermoplastic poly-ether-ester) Tradenames: Hytrel, Lomod, Pelprene and others which have the properties described herein so that when combined with a suitable ionomer the combined material can achieve the intended end functions described herein. A block copolymer containing both poly-ether and ester blocks. The best known example is poly-(tetramethyleneterephthalate-b-poly-oxytetramethyleneterephthalate).

Ionomer

IONOMER Trade name Surlyn, among others which have the properties described herein so that when combined with the suitable poly-ether-ester the combined material functions for its intended end results described herein. A copolymer of ethylene with 1–10% by weight methacrylic acid, which has been converted to methacrylate salt, often the sodium, magnesium or zinc salt, by neutralization with the appropriate base. The resultant ionic groups tend to aggregate to form domains which act as physical crosslinks for the polyethylene. However, the domains break down on heating, so the material may be melt processed as other thermoplastics. The copolymers are produced by the high pressure ethylene polymerization process and so are similar to low density polyethylene. The copolymer decreases crystallinity but consequent loss of stiffness is restored by the physical crosslinks. The material is more transparent than LDPE and shows better adhesion, which makes it useful as a layer in laminated co-extruded packaging films and in, therefore, homogenous mixing.

Reference is made to U.S. Pat. No. 5,496,291 all of the details of which are incorporated herein by reference thereto for a further disclosure of the ionomeric modified poly-ether-ester component of the material.

Poly-ether-esters are valuable materials because they have excellent low temperature properties (freezing) and are impervious to chemicals, oils and tissue. They have one serious negative, however, for many end-uses: They stretch 7× their length under low stress. For example, a tube one foot long will stretch to seven feet before breaking. Industrial goods such as bags, films, tubes, etc. readily warp out of shape and become unacceptable as end-use products. The present invention adds an ionomer to the composition to make useful, thin products.

Ionomers are somewhat like polyethylene in that they are useful as films because they are excellent for food wrapping, medical and pharmaceutical packing and are impervious to most oils and chemicals. Like polyethylene, they puncture readily and only stretch 3× before fracture.

A common use is a coating over stronger materials and are frequently used as a co-extrusions on nylon and other films to provide heat sealing.

The invention makes use of the fact that poly-ester-ethers and ionomers can be selected which melt at the same temperature (191° C.) or at sufficiently close temperatures. Instead of a coating, the invention mixes them together. In this way, the negatives of the two materials could be adjusted in a variety of ways to make new materials that are stronger than the ionomers, and less stretchy than the poly-ether-esters.

Combining the two materials as described also reduces another major limitation of the poly-ester-ethers (P.E.E.). They can absorb excessive moisture depending upon temperature and humidity. In the case of P.E.E. use in autoclaved (steam sterilized) medical tubing for example, the moisture pick-up makes the tubing unacceptable for further processing. Adding 5% to 7% ionomer to the composition reduces the moisture absorbance to less than 1% by weight. A level comparable to medical grade PVC and well within the limits required for TCD® to welding.

For forming the material of this invention the following process may be used. The individual materials are fed separately in pellet form into a single screw extruder. Other forms of extruders could be used satisfactorily but a single screw is sufficient and simpler to control. The materials in pellet streams are mixed to the required ratios and fed into the extruder. Extrusion rates of 10 to 250 lbs per hour are practical at melt temperatures of 180° C. to 200° C., with 191° C. being ideal. The melt is fed through a sizing die and liquid quenched as it exits the die for accuracy and handling purposes.

A typical extruder heating and mixing profile would involve feeding the materials, such as in pellets, from individual feed hoppers into the extruder where the feed zone of the extruder is at 300° F. The material would then pass to a compression zone at 350° F. The materials would then pass into a melting zone at 375° F. Finally, the material would be extruded into the desired shapes. Techniques such as conventionally used for PVC could then be used for forming the end products.

Various types of silica may be incorporated in the material in accordance with this invention. For example, silica oil makes the material less fracturable and adds lubricity/toughness to the resultant material. Preferably the silica oil would be present in an amount of 5%–10% by weight of the combined composition and more preferably 7%–8% by weight. Another form of silica is colloidal silica dioxide which would be used as a strengthening agent as an admix to the ionomeric modified poly-ether-ester. The colloidal silica dioxide is preferably an amorphous (pharmaceutical grade). An example of such material is CAB-O-SIL® from Cabot Corporation which is a fumed silica in white, free-flowing powder form of extremely high purity. Such material has been used for pharmaceutical applications. Preferably, the colloidal silica dioxide would be incorporated into the final composition as 1%–3% by weight of the composition. Such small admix is an excellent choice to increase the strength of the material.

By adjusting the mixtures of poly-ether-ester, ionomer and silica it is possible to optimize the polymer-end use properties, such as tensile strength, fracture strength, elongation, optical clarity, thermal welding performance and R.F. sealing performance.

In a general way, one might think of a silica, ionomer, and poly-ether-ester composition of matter in a similar way as the weaving of various nature and man-made fibers to achieve desired blending for clothing. The mixture or composition is not a chemical interaction, but rather an interaction of mechanical properties. The mixture of poly-ether-ester ionomers and silica is not an atomic chemical reaction but a molecular mix. The poly-ether-ester provides the characteristic of elongation. The ionomer provides clarity and fracturability. The silica provides strength. One can select the desired blend of properties for adjusting the ingredients. The invention thus lends itself in one case to use the poly-ether-ester as a way of avoiding the plasticizer, di-octyl-phlate, required to soften PVC. In another case, however, various additions of an ionomer can be used to create fracture characteristics such as the rupturing of sealed diaphragms required for sterile connection technology.

Depending upon the end properties desired the blend of poly-ether-ester, ionomer and silica could thus be from 75% to 99% by weight poly-ether-ester, mixed with from 0.5% to 50% by weight ionomer, mixed with 1% to 10% by weight silica where the three ingredients are mechanically mixed together to obtain the desired blend of characteristics. When used for products such as tubing, broad ranges for these products are from 75% to 99% by weight poly-ether-ester, from 0.5% to 50% by weight ionomer and from 1% to 10% by weight silica. Preferred ranges are 75% to 90% by weight polyether-ester, 1% to 15% by weight ionomer and 5% to 10% by weight silica oil or 1% to 3% by weight colloidal silica dioxide. More preferred amounts of ionomer are 2% to 15% or 3% to 10% with 7% to 10% being most preferred. More preferred amounts of silica oil are 7% to 8% by weight. When used for products such as containers the ranges are from 50% to 99% by weight poly-ether-ester, from 1% to 50% by weight ionomer and the same amounts of silica as for tubing. Preferred ranges for products such as containers are from 75% to 90% by weight poly-ether-ester, from 7% to 15% (most preferably from 7% to 10%) by weight ionomer.

Figure 4:
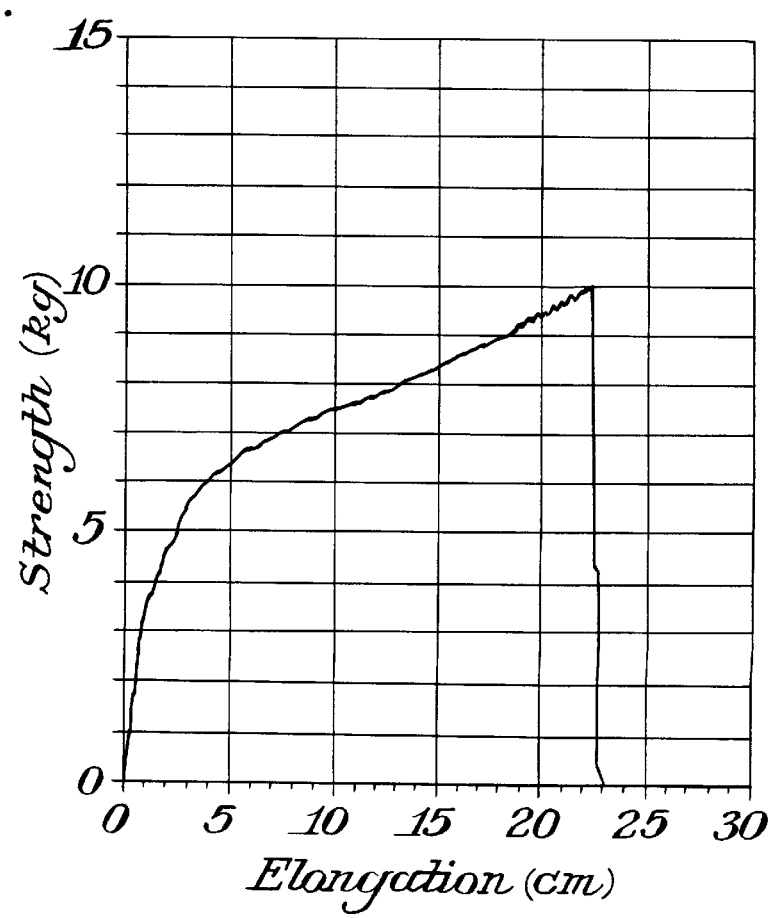

FIG. 1 illustrates a tube 10 made from an ionomeric modified poly-ether-ester containing silica in accordance with this invention. Tube 10 has characteristics which make it ideally suited for its intended uses as an improved replacement for conventional PVC. For example, using a modification ratio of 3% to 10% by weight, the material will provide seal strengths in excess of 60 psi internal pressure as indicated in Table 1. The material will weld to itself with tensile strengths of 10 kgs for tubes of 5.4 mm outside diameter and a wall thickness of 0.7 mm as indicated in FIG. 4. Such tensile strengths can even exceed 10 kgs.

The welds for tube 10 can be reopened with the same ease as PVC by external finger pressure such as by squeezing.

There is no degradation such as the smoke or particulates characteristic of the 100% PVC with the material of this invention being generated at welding temperatures of 320° C. and exposure times of less than 1 second. The material of this invention can be steam or ETO sterilized without geometry changes. In particular the material will permit steam sterilization of itself and the tube contents without changing the sealing or welding conditions because of extremely low water (steam) adsorption or retention.

FIGS. 2, 2A and 2B illustrate use of this invention for urinary drainage application. As shown therein tubing 10 is utilized as the tubing which leads from an operative site, such as the patient 12 to a urinary bag 14. Urinary bag 14 may also be made of the ionomeric modified poly-ether-ester and silica combination of this invention. In use for urinary drainage application the invention has advantages over 100% medical grade (Class VI) di-octyl-phlate (DOP) plasticized PVC. For example, since there is no plasticizer with the material of this invention there is no leaching of plasticizer into the bag solutions as is common with 100% PVC. Additionally, after conventional PVC has leached its DOP, large volumes of PVC particulates are released. This does not happen with the material of this invention.

For urinary drainage application the full bag 14 is to be separated from the patient discharge line so that it can be replaced by a fresh bag. A preferred practice of accomplishing such substitution would be to use the total containment sterile connection device as described in U.S. Pat. Nos. 5,141,592; 5,156,701; 5,158,630; 5,209,800; 5,244,522 and 5,279,685 the details of which are incorporated herein by reference thereto. Such sterile connection device is referred to as TCD®. By using such techniques the discharge line is disconnected at any suitable location such as the location 16. This leaves a portion of the tubing extending from the operative site or patient 12. A new bag 14 is attached by welding a tubing 10 leading from the new bag so that the tube sections become integral at the weld connection at location 16. The full or used bag is completely sealed and set aside to be weighed for total volume and volume per unit time for determining the discharge rate. The sealing is advantageously accomplished because of the sealing characteristics of the ionomeric modified poly-ether-ester and silica material. FIG. 2A, for example, shows a seal 18 formed at the top of bag 14 and FIG. 2B shows a seal 20 formed at the discharge line of bag 14 by use of TCD®.

The full bag 14 and its contents can be disposed of as a sealed biological waste. Alternatively, the bag 14 can be suspended on a standard bag holding pole over a commode and the bottom seal 20 can be opened by use of the fingers and thumb as is possible from seals formed by the total containment sterile discharge connection use for PVC. The bag contents will not drain at this point because of lack of air displacement. When the top seal 18 is opened again by finger pressure if desired the bag contents will immediately begin draining. The use of these two seals 18,20 created by the total containment device have the advantage of draining the bag contents without tools and in the manner that the bag contents do not contact the nurse's hands. This feature is of extreme importance to protect the nurses from contamination and also prevents cross-contamination with a hospital ICU facility. Cross-contamination in ICUs is currently a major problem.

The new or empty and sterile bag 14 is welded to the patient line at welding site 16 immediately after removing the full bag to provide uninterrupted flow from the patient.

An advantage of the ionomeric modified poly-ether-ester and of such material containing silica is its ability to be effectively welded to conventional PVC. This is important because it permits the replacement of some of the PVC components with the new material. Thus, for example, in CAPD usage it is necessary to remove a used filled bag for replacement by a new empty bag. The conventional PVC tubing could be cut and tubing from the new material could be welded to the remaining PVC tube segment. The new material components could thus gradually replace their PVC counterparts. FIG. 3 demonstrates the weld strength of PVC tubing to ionomeric modified poly-ether-ester tubing.

FIGS. 3 and 4 are graphs illustrating the ability of the weld to pop open. As shown therein with use of the ionomeric modified poly-ether-ester (FIG. 4) the unsealing characteristic is accomplished with approximately the same ease as in PVC tubing welded to the modified poly-ether-ester tubing (FIG. 3).

FIGS. 5–6 illustrate use of the invention with respect to peritoneal dialysis (CAPD). FIG. 5 represents the prior art practices wherein a tube 22 is utilized made from 100% PVC. In such applications PVC is the material of choice of the health care industry for both the tubing and the solution bags 24. The reasons for favoring PVC are that its long standing use started early in the 1960s. Additionally, there is film clarity for visual clarification and PVC provides low cost and abundant supplies. The PVC used for peritoneal dialysis, however, must undergo bulk sterilization after packaging to insure sterility to the entire product offering prior to patient use. Steam sterilization (250° F. for thirty minutes) of 100% PVC in contact with dialysis solutions causes several serious problems. For example, the PVC plasticizer (di-octyl-phlate), DOP, leaches out of the PVC composition during steam sterilization and into the dialysis solution. DOP is under suspicion of being a low level carcinogen. A further product that is after DOP leaching the residual PVC composition is vulnerable to particulates being formed and entering the dialysis solution which in turn enters the patient's body. Further, water adsorption (from the steam sterilization) into the patient tubing and bags reduces the plastic strength by approximately 50% causing bag leakage and sterility failures. FIG. 5 illustrates the conventional practice of using PVC as a material for the tubing 22 and bag 24 wherein the solution 26 in the bag 24 is caused to flow through tubing 22 to the patient's site 28. Steam sterilization takes place in chamber 30. FIG. 5 also illustrates the separation and connection area 32 used for replacing solution bags by separating and then rejoining the PVC transfusion line 22.

FIG. 6 illustrates use of the material of this invention for the tube 10 and bag 14. This material overcomes the PVC problems in several ways without sacrificing the positive attributes of PVC. With the material of this invention there is no plasticizer, thus leaching is not a problem. The material also does not form particulates and is impervious to steam sterilization to retain 100% of its strength. The ionomeric modified poly-ether-ester has another positive feature that is unique to sterile connection devices that use a heated blade to achieve sterility. The material does not make smoke. Conversely, when PVC is heated using the TCD™ instrument of the aforenoted patent the plasticizer DOP evolves as fine aerosol droplets that gives the appearance of smoke. Means must be provided therefore to contain and dispose of the smoke harmlessly. Since the material of this invention has no plasticizer, no smoke is formed using the TCD™ process.

The use of the total containment device TCD™ has a more significant potential for peritoneal dialysis, however, in that steam sterilization and its problems can be avoided entirely. For example, the ionomeric modified poly-ether-ester containing silica consumable bags, tubes, etc. can be bulk sterilized by ethylene oxide at the point of manufacture. The solutions can also be sterilized in bulk storage tanks and made ready to fill the previously sterilized bags. Using the TCD™ the sterile solutions can be fed to the sterile consumable thus avoiding steam sterilization. FIG. 6 illustrates by use of the connect/disconnect areas 16 how the ionomeric modified poly-ether-ester of this invention for tubing 10 can be used for replacing bags thereby resulting in a plurality of filled bags 34 with the unfilled bags 36 ready to be connected by weld 16 which would join its tubing 10 to the tubing leading from the sterile solution container 14.

FIG. 7 illustrates use of the invention for blood processing. In this application the use of ionomeric modified poly-ether-ester materials has several end-use advantages. Since the material has no plasticizers the problems of plasticizer leaching into the blood are eliminated. The problems of mixing and matching of various sources of blood bags and tubing are also eliminated. Mixing and matching is viewed by the FDA as a health threat when bags and tubing of unknown source and composition are introduced into blood centers because of cost or availability. Eventually the material can be frozen and retain its flexibility, thus avoiding brittle fracture.

Mix and match is considered by the FDA as a serious quality control and safety problem in the blood processing industry. Mix and match is an expression used to describe the chaotic situation in blood banks brought on by economics. Blood banks buy blood bags and tubing strictly on price without too much regard to source. Global dumping practices, questionable polymer compositions and tube size variation all contribute to the problem. In order to exercise a measure of control the FDA would prefer to be able to mandate a set of regulations regarding tube quality and be able somehow to exclude tubing that does not meet the FDA criteria.

The material of this invention meets this requirement again because the material contains no plasticizers. Commonly used medical grade PVC contains up to 40% DOP as a plasticizer that vaporizes to a smoke when the welding temperature exceeds 200° C. By using what amounts to a small smoke detector in the TCD™ the instrument can detect the smoke generation and refuse to complete the welding cycle. Specifically, prior to making a weld the tube ends are made to touch the wafer for one second. If no smoke is generated the process will proceed to make a weld. If smoke is detected the instrument will abort. In this way, the mixture will mix and match problem so important to the FDA and safety of the nation's blood supply can be avoided.

Use of the material of this invention has a positive effect when used in conjunction with TCD™ in that tube sealing (separating) can be accomplished in the TCD™ as well as connections. Blood banks have the capability of sealing off tubing by radio frequencies (RF) sealers. Because of the radio frequency, however, the equipment is normally located away from the blood processing areas and shielded for safety (booths). The inconvenience of going to a sealer encourages people to make poor seals via hot plates and bunsen flames rather than taking the bags to the RF sealer. Use of the TCD™ avoids this problem. The TCD™ is located in the work place. The use of the TCD™ in blood banking has another important advantage. It is called "un-bundling" and means complete flexibility to disconnect and connect blood bags at will. Without the sterile connection technology afforded by TCD™ this concept is not possible. For example, when blood is collected at the blood banks it is not known at that time what blood fractions will be required to meet end use needs. To overcome this unknown all blood is collected in bag sets. That is, a primary blood bag and four satellite bags are sent as a sterilized set. This is illustrated in FIG. 7 wherein the blood supply needle 38 has its tubing 10 leading to primary blood bag 40 with tubing 10 also leading to the four satellite bags 42 each of which has its tubing 10 connected to the main tubing by the TCD connect or disconnect location 16.

After the blood is centrifuged the fractions are expressed over into various component bags and sealed off. Once sealed off the bags can not be re-entered without compromising sterility. In the practice of this invention all of the tubing 10 and the various bags 40,42 would be made of the ionomeric modified poly-ether-ester containing silica material.

If, for example, only whole blood is needed, the four unused satellite bags 42 are separated and discarded. At approximately $2.00 per bag this loss is keenly felt by the blood bank. Moreover, if the bags are used and sealed it is not possible to enter the bags to enhance the cell life by the addition of stabilizers, nutrients or enhancers without compromising sterility.

The use of the TCD™ has made "un-bundling" possible. The TCD™ is designed to sterilely disconnect and connect sterile containers at will thereby providing the medical profession a desired level of flexibility and at lower consumable costs.

The use of the ionomeric modified poly-ether-ester containing silica materials would be non-pyrogenic to human tissue through wide spread use of permanently placed interval sutures. For this reason, the poly-ether-ester material is approved by the FDA for internal human use and is ideal for blood bags.

FIGS. 8–9 relate to use of the invention for chemotherapy. FIG. 8 illustrates the conventional practice to administer chemo-therapeutic drugs for cancer patients by introducing the drugs via syringe 44 or a pump into the intravenous transfer tubing 22. Solution would also flow into PVC tubing 22 from PVC bag 24. The syringe port is a convenient entry site for bacteria. For patients whose immune system is depressed from the therapy bacteria entry is life threatening. This problem can be eliminated by the use of the TCD™ instrument.

Use of the TCD™ instrument in combination with the ionomeric modified poly-ether-ester containing silica material for chemotherapy application has several end use advantages. Since there is no plasticizers involved, the danger of plasticizer leaching into the patient is eliminated. Since there are no particulates this form of contamination into the patient's blood stream is also eliminated. The poly-ether-esters are already used widely within humans for sutures and arterial repair. They present no pyro-genic defects therefore for human use.

FIG. 9 illustrates use of the inventive material for bag 14 and tubing 10. As shown therein at the normal entry port location 46 a ionomeric modified poly-ether ester containing silica tube 48 is spliced into the line 50 also made of that material and is terminated with a closed (sealed) distal end 52. The syringe 44 or pump is sterilely enclosed in a sheath 54 and terminated with a closed sealed distal end.

Making a sterile connection via the TCD™ the connection is totally contained. No bio-burden can enter the patient and no chemotherapy agents can escape outside the system. The syringe can also be sterilely disconnected by the TCD™ when the procedure is complete.

FIG. 10 illustrates use of the invention for parenteral feeding. For cancer patients who have suffered alimentary tract removal because of the cancer, feeding is accomplished by liquid nutrients fed into the patient's blood stream by way of a tube inserted into a sub-clavian vein and then into the heart.

Long term implantation of PVC tubing is also a problem. PVC plasticizer extraction directly into a patient's blood stream is particularly troublesome.

As pointed out in *Biocompatible Polymers, Metals and Composites* by M. Szycher, Sponsored by Society of Plastics Engineers Inc., Techmonic Publishing Co. 1983, flexible PVC compounds can contain up to 40% plasticizer. While the chosen material is very carefully selected for its high purity and low toxicity, it can be extracted from PVC by contact with some fatty substances, such as by blood or the digestive system. When contact times are short there is no difficulty, but for a number of applications in which PVC may be in contact with the patient's system for longer periods extraction of plasticizer is much less acceptable. Stiffening of PVC due to plasticizer being extracted may cause patient's considerable discomfort when a feeding or wound drainage tube is removed after prolonged use. Blood stored in PVC bags or flowing through PVC tubes for long periods will also extract plasticizer. While that most commonly used, DEHP, has been shown to be of low toxicity it is naturally desirable to avoid any extra burden on a patient's system. This is obviously more important for those needing regular hemodialysis for blood transfusions.

The use of ionomeric modified poly-ether-ester containing silica materials for tubing is beneficial in two ways. There is essentially no leaching of plasticizers into the patient's system from the implanted tube. Additionally, the poly-ether-ester material is compatible with the TCD™ for making sterile connects and disconnects from the implant. FIG. 10, for example, illustrates the use of a bag 14 made from the inventive material supplying the liquid nutrients through tubing 10 made from the inventive material into the patient's heart 56. By use of the TCD™ a sterile connect/disconnect procedure 16 can be effectively used to replace the bag 14 with a new bag 14.

The invention may also be used for cell culturing and particularly has applications in connection with the TCD™ in biotechnology. In such applications the inventive material would be used as tubing from the reactor.

In addition to the above described uses of the invention the ionomeric modified poly-ether-ester containing silica may also be used in food processing particularly as tubing for fluids and semi-solids and as the material for making sheets and films for bacterial and virus extrusion. When used as sheets or films, the sheet could be draped over the patient and the surgeon would cut through the sheet into the patient. The ionomeric modified poly-ether-ester containing silica may in effect be used as a suitable replacement for PVC in virtually all uses of PVC.

Although the above description has been directed to the provision of a combination of poly-ether-ester and an ionomer and silica, the invention may also be practiced by further incorporating a minor amount of PVC in the mixture. Reference is made to co-pending application Ser. No. 08/742,046 filed Nov. 1, 1996, all of the details of which are incorporated herein by reference thereto. The copending application describes a material made from a combination of poly-ether-ester and ionomer and a minor amount of PVC. The present invention could thus be practiced by incorporating into the various mixtures described in the copending application an additional minor amount of silica. Where examples are given in the copending application of combinations of material with specific weight percentages, those examples would be modified by adding to those combinations the amounts of silica described herein which would proportionately decrease the amounts of the other ingredients.

What is claimed is:

1. A plastic tubing for conveying fluid between a first location and a second location, said tubing being made from an ionomeric modified poly-ether-ester material containing from 0.5% to 50% by weight ionomer, said poly-ether-ester being a block copolymer containing both poly-ether and ester blocks modified by an ionomer, said ionomer being a copolymer of ethylene with 1–10% by weight methacrylic acid converted to methacrylate salt, said poly-ether-ester and said ionomer both individually and in combination being plasticizer-free, said material containing a minor amount of silica, said tubing being capable of being welded to itself to form a seal which resists opening at internal pressure up to 60 psi, and said seal being capable of being opened under external finger pressure.

2. A tubing of claim 1 in combination therewith an assembly for transferring a fluid between a first location and a remote container by means of said tubing.

3. A tubing of claim 2 wherein said tubing is in flow communication with a container whereby said tubing may be sealed to close flow communication and then said tubing may be cut to permit said container to be replaced by a further container having further tubing mounted thereto with said further tubing being weldable to said tubing so that upon the connection of said tubing to said further tubing and the later opening of said seal a flow communication is established between said further container and said tubing.

4. A tubing of claim 3 wherein said further tubing is made from said ionomeric modified poly-ether-ester material containing a minor amount of silica.

5. A tubing of claim 4 wherein said container and said further container are made from said ionomeric modified poly-ether-ester material containing 1–50% by weight ionomer.

6. A tubing of claim 5 wherein said ionomeric modified poly-ether-ester material of said tubing contains 2–15% by weight ionomer.

7. A tubing of claim 2 wherein said silica is silica oil, and said material contains from 5% to 10% by weight silica.

8. A tubing of claim 7 wherein said container is made from said material which contains from 5% to 10% by weight silica in the form of silica oil.

9. A tubing of claim 8 wherein said material for said tubing and said container contains 7% to 8% by weight of silica oil.

10. A tubing of claim 2 wherein said assembly is a blood processing assembly, said blood processing assembly including a blood supply needle and a blood collecting container, and said tubing being in flow communication with said needle and said blood collecting container.

11. A tubing of claim 10 wherein said blood collection container is a primary blood container, a plurality of satellite containers, and said tubing being in flow communication between said primary blood container and said satellite containers.

12. A tubing of claim 2 wherein said silica is colloidal silica dioxide, said material of said tubing containing from 1% to 3% by weight colloidal silica dioxide.

13. A tubing of claim 12 wherein said container is made from said material which contains from 1% to 3% by weight of silica in the form of colloidal silica dioxide.

14. A tubing of claim 2 wherein said material contains from 7% to 10% by weight ionomer.

15. A tubing of claim 2 wherein said tubing is welded to a polyvinylchloride tube section.

16. A tubing of claim 2 wherein said assembly is a peritoneal dialysis assembly including a dialysate container for being mounted at a location remote from the patient, and said tubing being connected to and in fluid communication with said container for permitting flow of fluid between said container and the patient.

17. A tubing of claim 2 wherein said assembly is a urinary drainage assembly, said urinary drainage assembly including a urinary container for being remote from the patient, and said tubing being in flow communication with said container for conveying urine from the patient to said container.

18. A tubing of claim 2 wherein said assembly is a chemotherapy assembly, said chemotherapy assembly including a solution container, said tubing being in flow communication with said solution container for leading to a patient to deliver the solution to the patient, and a drug introducing assembly communicating with said tubing to introduce a drug into the solution.

19. A tubing of claim 2 wherein said assembly is a parenteral feeding assembly, said parenteral feeding assembly including a liquid nutrient container, a tube for insertion into the sub-clavian vein of a patient, and said tubing being in flow communication with said container and said tube.

20. A tubing of claim 2 wherein said assembly is a cell culturing assembly, said cell culturing assembly including a reactor, and said tubing leading from said reactor.

21. A tubing of claim 2 wherein said assembly is a food processing assembly having said tubing for conveying the food being processed.

22. A tubing of claim 2 wherein said container is made from an ionomeric modified poly-ether-ester material containing from 1% to 50% by weight ionomer.

23. A tubing of claim 2 wherein said poly-ether-ester and said ionomer have generally the same melting temperature to facilitate their mixing in the making of said tubing.

24. A tubing of claim 2 wherein said material also includes a minor amount of polyvinylchloride.

25. A tubing of claim 24 wherein said material of said tubing contains a combination of from 75% to 99% by weight poly-ether-ester and from 1% to 25% by weight ionomer, and silica in the form of colloidal silica dioxide being added to said combination in an amount of from 1% to 3% by weight of said combination.

26. A tubing of claim 24 wherein said material of said tubing contains a combination of from 75% to 99% by weight poly-ether-ester and from 1% to 25% by weight ionomer, and silica in the form of silica oil being added to said combination in an amount of from 5% to 10% by weight of said combination.

27. A tubing of claim 24 wherein said material additionally includes a minor amount of polyvinylchloride.

* * * * *